(12) United States Patent
Hu

(10) Patent No.: US 7,423,044 B2
(45) Date of Patent: Sep. 9, 2008

(54) PYRIMIDINE DERIVATIVES USEFUL IN THE TREATMENT OF INSULIN RESISTANCE AND HYPERGLYCEMIA

(75) Inventor: Baihua Hu, Audubon, PA (US)

(73) Assignee: Wyeth, Madison, NJ (US)

( * ) Notice: Subject to any disclaimer, the term of this patent is extended or adjusted under 35 U.S.C. 154(b) by 549 days.

(21) Appl. No.: 10/655,471

(22) Filed: Sep. 4, 2003

(65) Prior Publication Data

US 2004/0110780 A1 Jun. 10, 2004

Related U.S. Application Data

(60) Provisional application No. 60/408,506, filed on Sep. 5, 2002.

(51) Int. Cl.
C07D 239/34 (2006.01)
A61K 31/505 (2006.01)

(52) U.S. Cl. .................................. 514/269; 544/319
(58) Field of Classification Search ............... 544/319; 514/269

See application file for complete search history.

(56) References Cited

U.S. PATENT DOCUMENTS

| 5,298,527 A | 3/1994 | Grammenos et al. |
| 6,001,867 A | 12/1999 | Wrobel et al. |
| 6,699,896 B1 | 3/2004 | Malamas |
| 6,849,761 B2 | 2/2005 | Mayer et al. |

FOREIGN PATENT DOCUMENTS

| DE | 4029649 | * | 3/1992 |
| DE | 4034672 A1 | | 5/1992 |
| EP | 0685467 A1 | | 12/1995 |
| GB | 1585950 | * | 3/1981 |
| JP | 04-001192 | | 1/1992 |
| JP | 4-1192 | | 6/1992 |
| WO | WO 94/14771 | * | 7/1994 |
| WO | WO 01/32632 A2 | | 5/2001 |

OTHER PUBLICATIONS

Mitchell et al., CAPLUS Abstract 115:49608, 1991.*
Reaven, et al., "Nonketotic Diabetes Mellitus: Insulin Deficiency or Insulin Resistance?", American Journal of Medicine, (Jan. 1976), vol. 60, pp. 80-88.
Stout, Metabolism: Clinical & Experimental, (Dec. 1985), 34 (12 Suppl 1): 7-12, (Abstract).
Pyorala, et al., Diabetes/Metabolism Reviews, "Diabetes and Atherosclerosis: An Epidemiologic View", (1987), vol. 3, pp. 463-524.
Jarrett, R. J., et al Diabetes/Metabolism Review, "Cardiovascular Disease and Hypertension in Diabetes Mellitus", (1989), vol. 5, No. 7, 547-558.
Harris, et al., Diabetes in America, "Mortality From Diabetes", Chapter 29, pp. 1-48, (1985).
Defronzo and Ferrannini, Diabetes Care, "Insulin resistance.",(Mar. 1991), 14, 173-194 (Abstract).

Haring, Diabetalogia, "The insulin receptor: signalling mechanism and contribution to the pathogenesis of insulin resistance", (1991), 34, 848-861 (Abstract).
B.J. Goldstein, J. Cellular Biochemistry, "Protein-tyrosine phosphatases and the regulation of insulin action", (1992), 48, 33 (Abstract).
B.J. Goldstein, Receptor , "Reg. of insulin receptor signaling by protein-tyrosine dephosphorylation", (1993), 3, 1-15 (Abstract).
F. Ahmad and B.J. Goldstein Biochim. Biophys Acta , "Purification, identification and subcellular distribution of three predominant protein-tyrosine phosphatase enzymes in skeletal muscle tissue", (1995), 1248, 57-69 (Abstract).
McGuire, et al., Diabetes, "Abnormal Regulation of Protein Tyrosine Phosphatase Activities in Skeletal Muscle of Insulin-Resistant Humans", (1991), vol. 40, 939-942.
Meyerovitch, et al., J. Clinical Invest., "Hepatic phosphotyrosine phosphatase activity and its alterations in diabetic rats", (1989), vol. 84, 976-983 (Abstract).
Sredy, et al Metabolism: Clinical & Experimental, "Insulin resistance is associated with abnormal dephosphorylation of a synthetic phosphopeptide corresponding to the major autophosphorylation sites of the insulin receptor", 44, 1074-1081 1995 (Abstract).

(Continued)

Primary Examiner—Deepak Rao
(74) Attorney, Agent, or Firm—Fish & Richardson P.C.

(57) ABSTRACT

This invention provides compounds of Formula I having the structure:

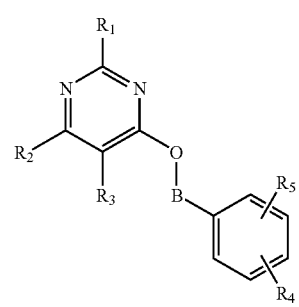

I wherein:
B is alkyl of 1-4 carbons or alkoxy of 1-4 carbons;
$R_1$ is aryl or Het optionally substituted with $R_6$;
$R_2$ and $R_3$ are each independently, alkyl of 1-4 carbons, $CF_3$, aryl or Het substituted with $R_6$, or $R_2$ and $R_3$ are combined to form a cycloalkyl or heterocyclic ring optionally substituted with alkyl, benzyl, or acyl;
$R_4$ and $R_5$ are each independently, hydrogen, halogen, alkyl of 1-4 carbons, $CO_2R_7$, $SO_2NHR_7$, $CONHR_7$, CN, $NO_2$ or $CF_3$;
$R_6$ is hydrogen, halogen, $NO_2$, alkyl of 1-4 carbons, alkoxy of 1-4 carbons, alkylcarbonyloxy of 2-7 carbon atoms, alkylcarbonyl of 2-7 carbon atoms, $CF_3$, or COOH; and
$R_7$ is hydrogen, alkyl of 1-4 carbons, or alkylaryl where aryl group is substituted with $R_6$; or a pharmaceutically acceptable salt thereof, which are useful in treating metabolic disorders related to insulin resistance or hyperglycemia.

23 Claims, No Drawings

OTHER PUBLICATIONS

Thomson Derwent on STN Abstract—Patent No. JP-04001192 A, Appl. 190JP-0100824, Apr. 17, 1990.

Thomson Derwent on STN Abstract—Patent No. DE-4034762A, Appl. 199DE-4034762, Nov. 2, 1990.

Goldstein, Barry. "Hot Topic: Protein-Tyrosine Phosphatases: Emerging Targets for Therapeutic Intervention in Type 2 Diabetes and Related States of Insulin Resistance." Journal of Clinical Engineering & Metabolism, 87(6), 2474-2480, 2002.

Lie, Gang et al. "Discovery and Structure-Activity Relationship of Oxalylarylaminobenzoic Acids as Inhibitors of Protein Tyrosine Phosphatase 1B." J. Med. Chem. 46, 2093-2103, 2003.

Cosford, Robyn. "Insulin Resistance, Obesity and Diabetes: The Connection." Journal of the Australian College of Nutritional and Environmental Medicine. 18:1, 3-10, Apr. 1999.

* cited by examiner

PYRIMIDINE DERIVATIVES USEFUL IN THE TREATMENT OF INSULIN RESISTANCE AND HYPERGLYCEMIA

This application claims priority from co-pending provisional application Ser. No. 60/408,506 filed on Sep. 5, 2002, the entire disclosure of which is hereby incorporated by reference.

FIELD OF THE INVENTION

This invention relates to pyrimidine derivatives useful as inhibitors of protein-tyrosine phosphatases (PTPases) and therapeutic compositions containing such compounds useful in the treatment of insulin resistance associated with obesity, glucose intolerance, diabetes mellitus, hypertension and ischemic diseases of the large and small blood vessels.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989, 5, 547; Harris et al, *Diabetes in America*, Chapter 29, pp 1-48, 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1-15; F. Ahmad and B. J. Goldstein *Biochim. Biophys Acta* 1995, 1248, 57-69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

JP 04001192 discloses the following compounds as agrochemical fungicides where R, $R_1$, $R_2$, $R_3$ are each hydrogen, alkyl or aryl; $R_4$ is halo, alkyl, alkoxy or nitro.

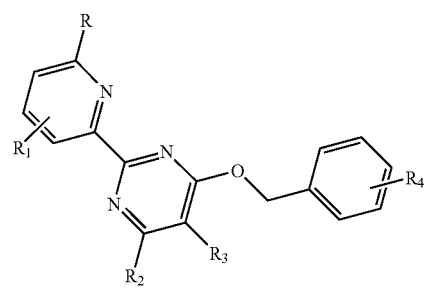

DE4034672 discloses compounds of the following formula as agrochemical fungicides where $R_1$, $R_2$, $R_3$, $R_4$ and $R_5$ are each hydrogen, alkyl, alkenyl, aryl, halogen, alkoxy, nitro or cyano.

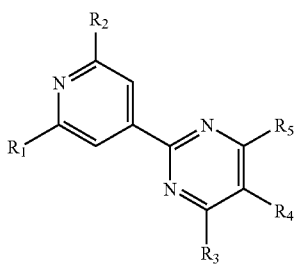

EP 513580 discloses compounds of the following formula as agrochemical fungicides where $R_1$ is alkyl or aryl; $R_2$, $R_3$ are each halogen or alkyl; $R_4$ is alkyl, alkoxy, alkenyl or alkynyl.

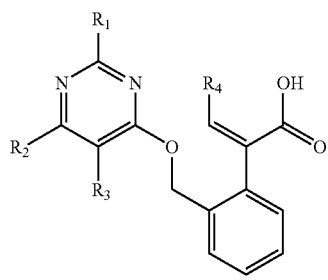

WO 9516677 discloses compounds of the following formula as angiotensin II antagonists where $R_1$, $R_2$ are each halogen, alkyl, alkenyl, alkynyl, alkoxy or aryl; $R_3$ is alkyl, alkoxy or arylalkyl; $R_4$ is tetrazolyl, cyano or carboxy.

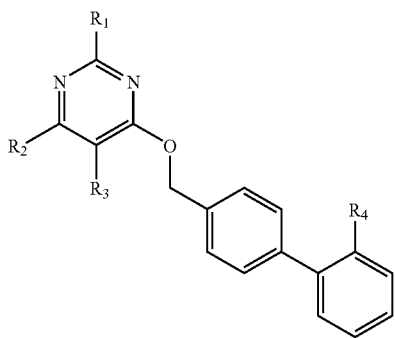

WO 0132632 discloses the following compounds as mGluR1 antagonists where $R_1$ is carbocyclyl or heterocylyl; $R_2$ is H, CN, $SCH_2CN$, halogen, alkylthio, alkoxy, alkylsulfonyl, alkylamino or alkylsulfinyl; $R_3$, $R_4$ are alkyl; $R_3R_4$ is a fused heterocycle, such as $S(CH_2)_3$, $CH_2O(CH_2)_2$, CH:CHS, or fused carbocycle, such as CH:CHCH:CH, $(CH_2)_4$; L is alkylene or a heteroalkylene linking group and $X_1$=O, NH.

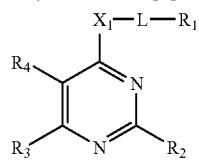

The compounds of this invention have been shown to inhibit PTPases derived from human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

SUMMARY OF THE INVENTION

The present invention relates to compounds of Formula I:

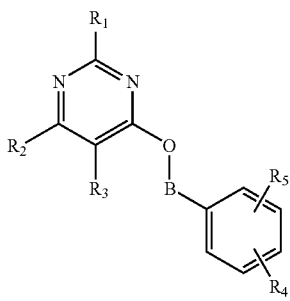

I wherein:
B is alkyl of 1-4 carbons or alkoxy of 1-4 carbons;
$R_1$ is aryl or Het optionally substituted with $R_6$;
$R_2$ and $R_3$ are each independently, alkyl of 1-4 carbons, $CF_3$, aryl or Het substituted with $R_6$, or $R_2$ and $R_3$ are combined to form a cycloalkyl or heterocyclic ring optionally substituted with alkyl, benzyl, or acyl;
$R_4$ and $R_5$ are each independently, hydrogen, halogen, alkyl of 1-4 carbons, $CO_2R_7$, $SO_2NHR_7$, $CONHR_7$, CN, $NO_2$, or $CF_3$;
$R_6$ is hydrogen, halogen, $NO_2$, alkyl of 1-4 carbons, alkoxy of 1-4 carbons, alkylcarbonyloxy of 2-7 carbon atoms, alkylcarbonyl of 2-7 carbon atoms, $CF_3$, or COOH; and
$R_7$ is hydrogen, alkyl of 1-4 carbons, or alkylaryl where aryl group is substituted with $R_6$ or a pharmaceutically acceptable salt thereof. The present compounds are useful in treating metabolic disorders related to insulin resistance or hyperglycemia.

DETAILED DESCRIPTION OF THE INVENTION

As used herein "alkyl" includes both straight chain as well as branched moieties. "Halogen" means bromine, chlorine, fluorine, and iodine. "Aryl" moieties as used herein include phenyl or naphthyl. "Het" includes monocyclic or bicyclic heterocycles of 5-10 ring atoms, having 1-4 heteroatoms selected from oxygen, nitrogen, and sulfur; wherein the heterocycle may be saturated or partially unsaturated.

Pharmaceutically acceptable salts of the present compounds can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, as well as other mixtures of the R and S stereoisomers and pharmaceutically acceptable salts thereof.

A preferred form of compounds of this invention comprises those having the Formula II:

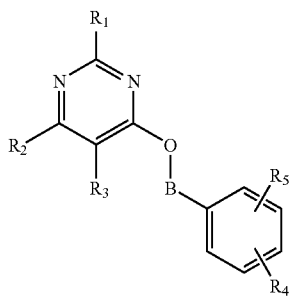

II wherein:
B is alkyl of 1-4 carbons;
$R_1$ is aryl or Het optionally substituted with $R_6$;
$R_2$ and $R_3$ are each independently, alkyl of 1-4 carbons, $CF_3$, aryl or Het substituted with $R_6$, or $R_2$ and $R_3$ are combined to form a cycloalkyl or heterocyclic ring optionally substituted with alkyl, benzyl, or acyl;
$R_4$, and $R_5$ are each, independently, hydrogen, halogen, $CO_2R_7$, CN, $NO_2$, or $CF_3$;
$R_6$ is hydrogen, halogen, $NO_2$, alkyl of 1-4 carbons, alkoxy of 1-4 carbons, $CF_3$, COOH; and
$R_7$ is hydrogen, alkyl of 1-4 carbons, or alkylaryl where the aryl group is substituted with $R_6$ or a pharmaceutically acceptable salt thereof.

Specifically preferred compounds of this invention are:
4-({[2-(4-chlorophenyl)-6-phenylpyrimidin-4-yl]oxy}methyl)benzoic acid;
2-(4-chlorophenyl)-4-[(4-fluorobenzyl)oxy]-6,7-dihydro-5H-cyclopenta[d]pyrimidine;
4-[(4-fluorobenzyl)oxy]-6-phenyl-2-pyridin-4-ylpyrimidine;
4-[(4-fluorobenzyl)oxy]-2-phenyl-6,7-dihydro-5H-cyclopenta[d]pyrimidine;
2-(4-chlorophenyl)-4-[(4-fluorobenzyl)oxy]-6-phenylpyrimidine;
4-{[(6-phenyl-2-pyridin-4-ylpyrimidin4-yl)oxy]methyl}benzoic acid;
4-{[(2,6-diphenylpyrimidin-4-yl)oxy]methyl}benzoic acid;
2-(3,5-dichlorophenyl)-4-[(4-fluorobenzyl)oxy]-6-isopropylpyrimidine;
6-benzyl-2-(3,5-dichlorophenyl)-4-[(4-fluorobenzyl)oxy]-5,6,7,8-tetrahydropyrido[4,3-d]pyrimidine;
4-[(4-fluorobenzyl)oxy]-6-isopropyl-2-(3-nitrophenyl)pyrimidine;
4-({[2-(3,5-dichlorophenyl)-6-isopropylpyrimidin-4-yl]oxy}methyl)benzonitrile;
4-({[6-benzyl-2-(3,5-dichlorophenyl)-5,6,7,8-tetrahydropyrido[4,3-d]pyrimidin-4-yl]oxy}methyl)benzonitrile;
4-({[6-isopropyl-2-(3-nitrophenyl)pyrimidin-4-yl]oxy}methyl)benzonitrile;
4-({[6-benzyl-2-(3-nitrophenyl)-5,6,7,8-tetrahydropyrido[4,3-d]pyrimidin-4-yl]oxy}methyl)benzonitrile;
2-(3,5-dichlorophenyl)-4-isopropyl-6-{[4-(trifluoromethyl)benzyl]oxy}pyrimidine;
6-benzyl-2-(3,5-dichlorophenyl)-4-{[4-(trifluoromethyl)benzyl]oxy}-5,6,7,8-tetrahydropyrido[4,3-d]pyrimidine;
4-isopropyl-2-(3-nitrophenyl)-6-{[4-(trifluoromethyl)benzyl]oxy}pyrimidine;
6-benzyl-2-(3-nitrophenyl)-4-{[4-(trifluoromethyl)benzyl]oxy}-5,6,7,8-tetrahydropyrido[4,3-d]pyrimidine;
4-({[2-(3,5-dichlorophenyl)-6-isopropylpyrimidin-4-yl]oxy}methyl)benzoic acid;
4-({[6-benzyl-2-(3,5-dichlorophenyl)-5,6,7,8-tetrahydropyrido[4,3-d]pyrimidin-4-yl]oxy}methyl)benzoic acid;
4-({[6-isopropyl-2-(3-nitrophenyl)pyrimidin-4-yl]oxy}methyl)benzoic acid;
4-({[6-Benzyl-2-(3-nitrophenyl)-5,6,7,8-tetrahydropyrido[4,3-d]pyrimidin-4-yl]oxy}methyl)benzoic acid; or pharmaceutically acceptable salts thereof.

The compounds of this invention can be readily prepared according to the following scheme from commercially available starting materials or starting materials which can be prepared using literature procedures. The scheme shows the preparation of representative compounds of this invention. It is also possible to make use of variants of these process steps, which in themselves are known to and well within the preparatory skill of the medicinal chemist. In the following reaction scheme, $R_1$, $R_2$, $R_3$, $R_4$, and $R_5$ are selected from groups defined above.

Briefly, the pyrimidine ring can be constructed by combing a β-keto ester with a benzamidine in the presence of base such as sodium methoxide or potassium carbonate. This reaction can be carried out in a polar solvent such as methanol, tetrahydrofuran, water or the like at a temperature of −15-30° C. for 0.5 to 50 hours. The resultant pyrimidine-4-ol can be alkylated with an appropriate alkylating agent alkyl halide or benzyl halide. In this alkylation potassium carbonate, sodium hydride, potassium tert-butoxide and the like can be used as a base, and dimethylformamide, tetrahydrofuran, acetone, acetonitrile and the like can be used as a solvent. The reaction is conveniently conducted at room temperature for 0.5 to 24 hours.

The compound represented by the above formula I where $R_4$ is acid can be prepared by a basic hydrolysis of the corresponding ester. In this reaction, lithium hydroxide, sodium hydroxide, potassium hydroxide and the like can be used as a base, and water or a mixture of water with methanol, tetrahydrofuran and the like can be used as a solvent. The final products can be purified by recrystallization, trituration, preparative thin layer chromatography, flash column chromatography on silica gel, or high performance liquid chromatography. Purification of intermediates can be achieved in the same manner. A salt is optionally produced by the addition of an acid or base, such as hydrogen chloride gas or hydrochloric acid.

Synthesis Scheme

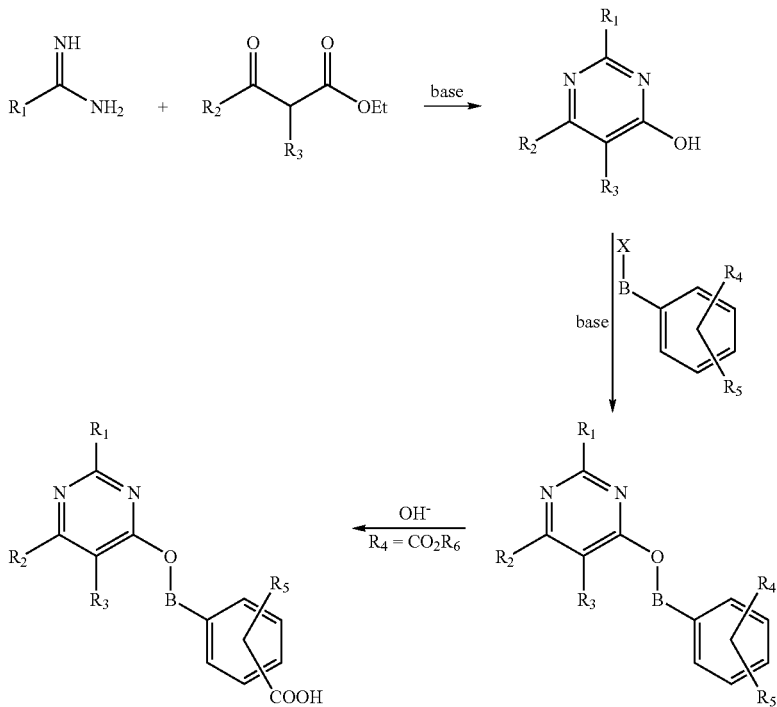

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedure which measures the inhibition of PTPase.

Inhibition Assay

Measurement of PTPase activity: The present compounds are assayed in an enzyme activity-based assay. PTP-1B is known to dephosphorylate phospho-peptides. This assay is a fluorescence intensity based kinetic assay, taking advantage of a non-peptidyl substrate, 6,8-difluoro-4-methylumbelliferyl phosphate (DIFMUP). When excited at 358 nm, the dephosphorylated product of DIFMUP emits at 450 nm.

The compounds of Examples 1-22 were analyzed as follows. The assay was conducted in black 384-well non-treated plates (Costar#3710). The assay buffer contained 50 mM 3,3-dimethyl glutaric acid, pH 7.0, 48 mM NaCl, 1 mM EDTA. Inhibitors were prepared as DMSO solution and diluted to desired concentrations using 50 mM HEPES, pH 7.4. PTP-1B was diluted to a 2.5 nM working stock using the assay buffer containing additional 0.001% (w/v) hydrogenated Triton X-100. DIFMUP was diluted to 40 μM using the assay buffer. 5 μl of inhibitor was first dispensed into assay plate. In cases of control reactions, 5 ml of the assay buffer was dispensed. This was followed by 25 μl of DIFMUP working stock. The reaction was then initiated by the addition of 20 μl of PTP-1B working stock. The final DIFMUP concentration was 20 μM ($\sim 1.6 \times K_m$). The final enzyme concentration was 1 nM and the detergent concentration was 0.0004% (w/v). Typical inhibitor concentrations were from 0.08 to 40 μM. The reaction progress was monitored continuously for 30 min.

Calculations: For data analysis, the last five data points were used to obtain a slope corresponding to the estimated steady-state velocity ($V_s$), and the overall progress curves were used to obtain the average velocity ($V_a$), by linear regression in both cases. The apparent final potency of inhibitor ($K_{iapp}$) was then calculated from $V_s$ data, using the standard hyperbolic inhibition equation. The $IC_{50}$ values were calculated from $V_a$ data using the sigmoidal inhibition equation. % Inhibition values were calculated from $V_a$ values of inhibitor at 40 μM, and the average $V_a$ value of control reactions.

TABLE 1

| Compound of Example | Activity Data | |
|---|---|---|
| | Kiapp | % Inhibition @ 40 μM |
| 1 | 1.67 | 100 |
| 2 | — | 10 |
| 3 | — | 11 |
| 4 | — | 12 |
| 5 | — | 11 |
| 6 | 7.21 | 56 |
| 7 | 2.97 | 99 |
| 8 | | 48 |
| 9 | | 55 |
| 10 | | 56 |
| 11 | | 34 |
| 12 | | 54 |
| 13 | | 55 |

TABLE 1-continued

Activity Data

| Compound of Example | Kiapp | % Inhibition @ 40 μM |
|---|---|---|
| 14 | | 64 |
| 15 | | 57 |
| 16 | | 52 |
| 17 | | 49 |
| 18 | | 51 |
| 19 | | 101 |
| 20 | | 100 |
| 21 | | 101 |
| 22 | | 93 |

Based on the results set forth above the compounds of this invention have been shown to inhibit PTPase activity (Table 1) and were therefore useful in treating metabolic disorders related to insulin resistance or hyperglycemia, typically associated with obesity or glucose intolerance. More particularly, the compounds of this invention are useful in the treatment or inhibition of type II diabetes, and in modulating glucose levels in disorders such as type I diabetes. As used herein, the term modulating means maintaining glucose levels within clinically normal ranges.

Effective administration of the compound of this invention may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

General Procedure 1 (for Intermediates): Pyrimidine Ring Formation:

The β-keto ester was dissolved in MeOH and benzamidine hydrochloride (2 equiv.) was added and the mixture was cooled down to 0-5° C. Sodium methoxide (0.5 M in MeOH, 2 equiv.) was added dropwise and the solution was warmed to room temperature and stirred for 48 h. The mixture was diluted with aqueous $NH_4Cl$ and the precipitate was collected. The solid was then washed with 0.2 N citric acid and aqueous $NaHCO_3$, dried in vacuo over $P_2O_5$ to give the pyrimidine. In a few cases there was no solid formed after diluted with aqueous $NH_4Cl$. The aqueous solution was then extracted with EtOAc. The combined extracts were washed with 0.2 N citric acid and aqueous $NaHCO_3$, dried over $MgSO_4$ and concentrated to give the pyrimidine.

Intermediate 1

2-(4-Chloro-phenyl)-6-phenyl-pyrimidin-4-ol

The title compound was prepared from 3-oxo-3-phenyl-propionic acid ethyl ester and 4-chloro-benzamidine hydrochloride according to general procedure 1. $^1$H NMR (DMSO-$d_6$, 400 MHz) δ 6.97 (s, 1H), 7.50-7.58 (m, 3H), 7.16 (d, J=8.5 Hz, 2H), 8.10-8.20 (m, 2 H), 8.30 (d, J=8.5 Hz, 2H), 12.50 (br s, 1H); MS: m/z (ESI) 283 (M+H).

Intermediate 2

2-(4-Chloro-phenyl)-6,7-dihydro-5H-cyclopentapyrimidin-4-ol

The title compound was prepared from 2-oxo-cyclopentanecarboxylic acid ethyl ester and 4-chloro-benzamidine hydrochloride according to general procedure 1. $^1$H NMR (DMSO-$d_6$, 400 MHz) δ 2.01 (tt, J=7.1, 7.1 Hz, 2H), 2.69 (t, J=7.1 Hz, 2H), 2.83 (t, J=7.1 Hz, 2H), 7.59 (d, J=8.5 Hz, 2H), 8.10 (d, J=8.5 Hz, 2H), 12.60 (br s, 1H); MS: m/z (ESI) 245 (M−H).

Intermediate 3

6-Phenyl-2-pyridin-4-yl-pyrimidin-4-ol

The title compound was prepared from 3-oxo-3-phenyl-propionic acid ethyl ester and isonicotinamidine hydrochloride according to general procedure 1. $^1$H NMR (DMSO-$d_6$, 400 MHz) δ 7.08 (s, 1H), 7.50-7.55 (m, 3H), 8.17-8.25 (m, 4 H), 8.88 (d, J=4.4 Hz, 2H), 10-12 (br s, 1H); MS: m/z(ESI) 250 (M+H).

Intermediate 4

2,6-Diphenyl-pyrimidin-4-ol

The title compound was prepared from 3-oxo-3-phenyl-propionic acid ethyl ester and benzamidine hydrochloride according to general procedure 1. $^1$H NMR (DMSO-$d_6$, 400 MHz) δ 6.92 (s, 1H), 7.50-7.65 (m, 6H), 8.15-8.20 (m, 2H), 8.26 (d, J=7.2 Hz, 2H), 12.80 (br s, 1H); MS: m/z (ESI) 247 (M–H).

Intermediate 5

2-Phenyl-6,7-dihydro-5H-cyclopentapyrimidin-4-ol

The title compound was prepared from 2-oxo-cyclopentanecarboxylic acid ethyl ester and benzamidine hydrochloride according to general procedure 1. $^1$H NMR (DMSO-$d_6$, 400 MHz) δ 2.01 (tt, J=7.2, 7.2 Hz, 2H), 2.69 (t, J=7.2 Hz, 2H), 2.84 (t, J=7.2 Hz, 2H), 7.45-7.60 (m, 3H), 8.07 (d, J=7.1 Hz, 2H), 12.40 (br s, 1H); MS: m/z (ESI) 213 (M+H).

Intermediate 6

2-(3,5-Dichloro-phenyl)-6-isopropyl-pyrimidin-4-ol

The title compound was prepared from 4-methyl-3-oxopentanoic acid ethyl ester and 3,5-dichloro-benzamidine hydrochloride according to general procedure 1. $^1$H NMR (DMSO-$d_6$, 400 MHz) δ 1.20-1.26 (m, 6H), 2.80-2.90 (m, 1H), 6.34 (s, 1H), 7.82(s, 1H), 8.18 (s, 2H), 12.50 (br s,1H); MS: m/z (ESI) 283 (M+H).

Intermediate 7

6-Benzyl-2-(3,5-dichloro-phenyl)-5,6,7,8-tetrahydro-pyrido[4,3-d]pyrimidin-4-ol The title compound was prepared from 1-benzyl-4-oxo-piperidine-3-carboxylic acid ethyl ester and 3,5-dichloro-benzamidine hydrochloride according to general procedure 1. $^1$H NMR (DMSO-$d_6$, 400 MHz) δ 2.70-2.90 (m, 4H), 3.20-3.50 (m, 4H), 3.70-3.90 (m, 2H), 7.10-7.50 (m, 6H), 7.83 (s, 1H), 8.12 (s, 2H), 12.70 (br s, 1H); MS: m/z (ESI) 386 (M+H).

Intermediate 8

6-Isopropyl-2-(3-nitro-phenyl)-pyrimidin-4-ol

The title compound was prepared from 4-methyl-3-oxopentanoic acid ethyl ester and 3-nitro-benzamidine hydrochloride according to general procedure 1. $^1$H NMR (DMSO-$d_6$, 400 MHz) δ 1.25 (d, J=6.9 Hz, 6H), 2.80-2.92 (m, 1H), 6.37 (s, 1H), 7.83 (t, J=8.0 Hz, 1H), 8.40 (dd, J=7.5, 2.3 Hz, 2H), 8.62 (d, J=7.5 Hz, 1H) 9.01 (s, 1H), 12.50 (br s, 1H); MS: m/z (ESI) 260 (M+H).

Intermediate 9

6-Benzyl-2-(3-nitro-phenyl)-5,6,7,8-tetrahydro-pyrido[4,3-d]pyrimidin-4-ol

The title compound was prepared from 1-benzyl-4-oxo-piperidine-3-carboxylic acid ethyl ester and 3-nitro-benzamidine hydrochloride according to general procedure 1. $^1$H NMR (DMSO-$d_6$, 400 MHz) δ 2.76 (s, 4H), 3.28 (s, 2H), 3.71 (s, 2H), 7.25-7.40 (m, 6H), 7.81 (t, J=8.0 Hz, 1H), 8.35-8.40 (m, 1H), 8.52 (d, J=8.0 Hz, 2H), 8.93 (s, 1H); MS: m/z (ESI) 363 (M+H).

Method A: General Procedure for O-alkylation of Pyrimidine

The pyrimidine (1 equiv.) and the alkylating agent (5~10 equiv.) were mixed in DMF (0.05-0.3M) and then treated with $K_2CO_3$ (5~10 equiv.). After stirring at rt for 1-24 h the mixture was poured into water. The precipitate which formed was collected and purified by preparative HPLC (The alkyl esters were converted to the corresponding acid without purifications).

Method B: General Procedure for Hydrolysis of Alkyl Ester

To a stirred solution of the alkyl ester (1 equiv.) in THF/MeOH/water (2:1:1) (0.01-0.5 M) was added LiOH (1-10 equiv.). The reaction was stirred at rt for 2-24 h. The reaction mixture was made acidic (pH 6) with glacial acetic acid, and the solid was collected. The product was purified by preparative HPLC and characterized by at least analytical LCMS. The experimental details for preparative HPLC and analytical LCMS are as following:

Preparative RP-HPLC Conditions:

Gilson Semi-Preparative HPLC system with Unipoint Software;

Column: Phenomenex C18 Luna 21.6 mm×60 mm, 5 μm; Solvent A: Water (0.02% TFA buffer); Solvent B: Acetonitrile (0.02% TFA buffer); Solvent Gradient: Time 0: 5% B; 2.5 min: 5% B; 7 min: 95% B; Hold 95% B 5 min;

Flow Rate: 22.5 mL/min;

The product peak was collected based on UV absorption and concentrated.

Analytical LCMS Conditions:

Hewlett Packard 1100 MSD with ChemStation Software;

Column: YMC ODS-AM 2.0 mm×50 mm, 5 μm, column at 23° C.;

Solvent A: Water (0.02% TFA buffer);

Solvent B: Acetonitrile (0.02% TFA buffer);

Gradient: Time 0: 5% B; 0.3 min: 5% B; 3.0 min: 90% B; Hold 95% B 2 min;

Flow rate 1.5 mL/min;

Detection: 254 nm DAD; API-ES Scanning Mode Positive 150-700; Fragmentor 70 mV.

EXAMPLE 1

4-({[2-(4-Chlorophenyl)-6-phenylpyrimidin-4-yl]oxy}methyl)benzoic acid

The title compound was prepared from 2-(4-chloro-phenyl)-6-phenyl-pyrimidin-4-ol (which was obtained in Intermediate 1) and methyl 4-(bromomethyl)benzoate according to Method A and Method B; $^1$H NMR (DMSO-$d_6$, 300 MHz) δ 5.61 (s, 2H), 7.26 (t, J=9.0 Hz, 2H), 7.45-7.70 (m, 8H), 8.25-8.35 (m, 2H), 8.55 (d, J=6.0 Hz, 2H); LC retention time 3.86 min; MS: m/z (ESI) 415 (M–H).

EXAMPLE 2

2-(4-Chlorophenyl)-4-[(4-fluorobenzyl)oxy]-6,7-dihydro-5H-cyclopenta[d]pyrimidine The title compound was prepared from 2-(4-chloro-phenyl)-6,7-dihydro-5H-cyclopentapyrimidin-4-ol (which was obtained in Intermediate 2) and 4-fluorobenzyl bromide according to Method A; $^1$H NMR (DMSO-$d_6$, 300 MHz) δ 2.09 (tt, J=7.5, 7.5 Hz, 2H), 2.83 (t, J=7.5 Hz, 2H), 2.95 (t, J=7.5 Hz, 2H), 5.58 (s, 2H), 7.25 (t, J=9.6 Hz, 2H), 7.50-7.65 (m, 4 H), 8.39 (d, J=8.6 Hz, 2H); LC retention time 3.53 min; MS: m/z (ESI) 355 (M+H).

EXAMPLE 3

4-[(4-Fluorobenzyl)oxy]-6-phenyl-2-pyridin-4-ylpyrimidine

The title compound was prepared from 6-phenyl-2-pyridin-4-yl-pyrimidin-4-ol (which was obtained in Intermediate 3) and 4-fluorobenzyl bromide according to Method A; $^1$H NMR (DMSO-$d_6$, 300 MHz) δ 5.72 (s, 2H), 7.50-7.70 (m, 6H), 7.93 (d, J=15.0 Hz, 2H), 8.30-8.37 (m, 2H), 8.37-8.41 (m, 2H), 8.80-8.90 (m, 2H); LC retention time 3.02 min; MS: m/z (ESI) 358 (M+H).

EXAMPLE 4

4-[(4-Fluorobenzyl)oxy]-2-phenyl-6,7-dihydro-5H-cyclopenta[d]pyrimidine

The title compound was prepared from 2-phenyl-6,7-dihydro-5H-cyclopentapyrimidin-4-ol (which was obtained in Intermediate 5) and 4-fluorobenzyl bromide according to Method A; LC retention time 3.26 min; MS: m/z (ESI) 321 (M+H).

EXAMPLE 5

2-(4-Chlorophenyl)-4-[(4-fluorobenzyl)oxy]-6-phenylpyrimidine

The title compound was prepared from 2-(4-chloro-phenyl)-6-phenyl-pyrimidin-4-ol (which was obtained in Intermediate 1) and 4-fluorobenzyl bromide according to Method A; LC retention time 4.35 min; MS: m/z (ESI) 391 (M+H).

EXAMPLE 6

4-{[(6-Phenyl-2-pyridin-4-ylpyrimidin-4-yl)oxy]methyl}benzoic acid

The title compound was prepared from 6-phenyl-2-pyridin-4-yl-pyrimidin-4-ol (which was obtained in Intermediate 3) and methyl 4-(bromomethyl)benzoate according to Method A and Method B; $^1$H NMR (DMSO-$d_6$, 300 MHz) δ 5.65 (s, 2H), 7.26 (t, J=8.8 Hz, 2H), 7.50-7.70 (m, 4H), 8.30-8.40 (m, 2H), 8.57 (d, J=4.9 Hz, 2H), 8.90 (d, J=4.9 Hz, 2H); LC retention time 2.79 min; MS: m/z (ESI) 382 (M−H).

EXAMPLE 7

4-{[(2,6-Diphenylpyrimidin-4-yl)oxy]methyl}benzoic acid

The title compound was prepared from 2,6-diphenyl-pyrimidin-4-ol (which was obtained in Intermediate 4) and methyl 4-(bromomethyl)benzoate according to Method A and Method B; $^1$H NMR (DMSO-$d_6$, 300 MHz) δ 5.62 (s, 2H), 7.25 (t, J=8.9 Hz, 2H), 7.49 (s, 1H), 7.50-7.70 (m, 12H); LC retention time 3.59 min; MS: m/z (ESI) 381 (M−H).

EXAMPLE 8

2-(3,5-Dichlorophenyl)-4-[(4-fluorobenzyl)oxy]-6-isopropylpyrimidine

The title compound was prepared from 2-(3,5-dichlorophenyl)-6-isopropyl-pyrimidin-4-ol (which was obtained in Intermediate 6) and 4-fluorobenzyl bromide according to Method A; $^1$H NMR (DMSO-$d_6$, 300 MHz) δ 1.27 (d, J=6.8 Hz, 6H), 2.90-3.10 (m, 1H), 5.54 (s, 2H), 6.88 (s, 1H), 7.24 (t, J=8.9 Hz, 2H), 7.57 (d, J=8.9, 8.5 Hz, 2H), 7.81 (s, 1H), 8.33 (s, 2H); LC retention time 4.45 min; MS: m/z (ESI) 391 (M+H).

EXAMPLE 9

6-Benzyl-2-(3,5-dichlorophenyl)-4-[(4-fluorobenzyl)oxy]-5,6,7,8-tetrahydropyrido[4,3-d]pyrimidine The title compound was prepared from 6-benzyl-2-(3,5-dichloro-phenyl)-5,6,7,8-tetrahydro-pyrido[4,3-d]pyrimidin-4-ol (which was obtained in Intermediate 7) and 4-fluorobenzyl bromide according to Method A; $^1$H NMR (DMSO-$d_6$, 300 MHz) δ 3.67 (br s, 4H), 4.24 (br s, 2H), 4.43 (br s, 2H), 5.64 (s, 2H), 7.25 (t, J=8.9 Hz, 2H), 7.60 (m, 3H), 7.83 (s, 1H), 7.95 (s, 1H); LC retention time 3.21 min; MS: m/z (ESI) 494 (M+H).

EXAMPLE 10

4-[(4-Fluorobenzyl)oxy]-6-isopropyl-2-(3-nitrophenyl)pyrimidine

The title compound was prepared from 6-isopropyl-2-(3-nitro-phenyl)-pyrimidin-4-ol (which was obtained in Intermediate 8) and 4-fluorobenzyl bromide according to Method A; LC retention time 4.01 min; MS: m/z (ESI) 368 (M+H)

EXAMPLE 11

4-({[2-(3,5-Dichlorophenyl)-6-isopropylpyrimidin-4-yl]oxy}methyl)benzonitrile

The title compound was prepared from 2-(3,5-dichlorophenyl)-6-isopropyl-pyrimidin-4-ol (which was obtained in Intermediate 6) and 4-cyanobenzyl bromide according to Method A; LC retention time 4.22 min; MS: m/z (ESI) 398 (M+H).

EXAMPLE 12

4-({[6-Benzyl-2-(3,5-dichlorophenyl)-5,6,7,8-tetrahydropyrido[4,3-d]pyrimidin-4-yl]oxy}methyl)benzonitrile The title compound was prepared from 6-benzyl-2-(3,5-dichloro-phenyl)-5,6,7,8-tetrahydro-pyrido[4,3-d]pyrimidin4-ol (which was obtained in Intermediate 7) and 4-cyanobenzyl bromide according to Method A; LC retention time 3.01 min; MS: m/z (ESI) 501 (M+H).

EXAMPLE 13

4-({[6-isopropyl-2-(3-nitrophenyl)pyrimidin-4-yl]oxy}methyl)benzonitrile

The title compound was prepared from 6-isopropyl-2-(3-nitro-phenyl)-pyrimidin-4-ol (which was obtained in Intermediate 8) and 4-cyanobenzyl bromide according to Method A; LC retention time 3.71 min; MS: m/z (ESI) 375 (M+H).

Example 14

4-({[6-Benzyl-2-(3-nitrophenyl)-5,6,7,8-tetrahydro-pyrido[4,3-d]pyrimidin-4-yl]oxy}methyl)benzonitrile The title compound was prepared from 6-benzyl-2-(3-nitro-phenyl)-5,6,7,8-tetrahydro-pyrido[4,3-d]pyrimidin-4-ol (which was obtained in Intermediate 9) and 4-cyanobenzyl bromide according to Method A; LC retention time 2.53 min; MS: m/z (ESI) 478 (M+H).

EXAMPLE 15

2-(3,5-Dichlorophenyl)-4-isopropyl-6-{[4-(trifluoromethyl)benzyl]oxy} pyrimidine The title compound was prepared from 2-(3,5-dichloro-phenyl)-6-isopropyl-pyrimidin-4-ol (which was obtained in Intermediate 6) and 4-(trifluoromethyl)benzyl bromide according to Method A; LC retention time 4.57 min; MS: m/z (ESI) 441 (M+H).

EXAMPLE 16

6-Benzyl-2-(3,5-dichlorophenyl)-4-{[4-(trifluoromethyl)benzyl]oxy}-5,6,7,8-tetrahydropyrido[4,3-d]pyrimidine The title compound was prepared from 6-benzyl-2-(3,5-dichloro-phenyl)-5,6,7,8-tetrahydro-pyrido[4,3-d]pyrimidin-4-ol (which was obtained in Intermediate 7) and 4-(trifluoromethyl)benzyl bromide according to Method A; LC retention time 3.49 min; MS: m/z (ESI) 544 (M+H).

EXAMPLE 17

4-Isopropyl-2-(3-nitrophenyl)-6-{[4-(trifluoromethyl)benzyl]oxy} pyrimidine

The title compound was prepared from 6-isopropyl-2-(3-nitro-phenyl)-pyrimidin-4-ol (which was obtained in Intermediate 8) and 4-(trifluoromethyl)benzyl bromide according to Method A; $^1$H NMR (DMSO-$d_6$, 300 MHz) δ 1.30 (d, J=6.8 Hz, 6H), 3.00-3.10 (m, 1H), 5.69 (s, 2H), 6.95 (s, 1H), 7.75-7.85 (m, 4H), 7.84 (t, J=8.1 Hz, 1H), 8.38 (t, J=8.1 Hz, 1H), 8.80 (d, J=7.8 Hz, 1H), 9.08 (s, 1H); LC retention 4.18 min; MS: m/z (ESI) 418 (M+H).

EXAMPLE 18

6-Benzyl-2-(3-nitrophenyl)-4-{[4-(trifluoromethyl)benzyl]oxy}-5,6,7,8-tetrahydropyrido[4,3-d]pyrimidine The title compound was prepared from 6-benzyl-2-(3-nitro-phenyl)-5,6,7,8-tetrahydro-pyrido[4,3-d]pyrimidin-4-ol (which was obtained in Intermediate 9) and 4-(trifluoromethyl)benzyl bromide according to Method A; LC retention time 2.95 min; MS: m/z (ESI) 521 (M+H).

EXAMPLE 19

4-({[2-(3,5-Dichlorophenyl)-6-isopropylpyrimidin-4-yl]oxy}methyl)benzoic acid The title compound was prepared from 2-(3,5-dichloro-phenyl)-6-isopropyl-pyrimidin-4-ol (which was obtained in Intermediate 6) and methyl 4-(bromomethyl)benzoate bromide according to Method A and Method B; LC retention time 4.11 min; MS: m/z (ESI) 415 (M-H).

EXAMPLE 20

4-({[6-Benzyl-2-(3,5-dichlorophenyl)-5,6,7,8-tetrahydropyrido[4,3-d]pyrimidin-4-yl]oxy}methyl)benzoic acid The title compound was prepared from 6-benzyl-2-(3,5-dichloro-phenyl)-5,6,7,8-tetrahydro-pyrido[4,3-d]pyrimidin-4-ol (which was obtained in Intermediate 7) and methyl 4-(bromomethyl)benzoate according to Method A and Method B; LC retention time 2.77 min; MS: m/z (ESI) 520 (M+H).

EXAMPLE 21

4-({[6-Isopropyl-2-(3-nitrophenyl)pyrimidin-4-yl]oxy}methyl)benzoic acid

The title compound was prepared from 6-isopropyl-2-(3-nitro-phenyl)-pyrimidin-4-ol (which was obtained in Intermediate 8) and methyl 4-(bromomethyl)benzoate according to Method A and Method B; LC retention time 3.40 min; MS: m/z (ESI) 394 (M+H).

EXAMPLE 22

4-({[6-Benzyl-2-(3-nitrophenyl)-5,6,7,8-tetrahydro-pyrido[4,3-d]pyrimidin-4-yl]oxy}methyl)benzoic acid The title compound was prepared from 6-benzyl-2-(3-nitro-phenyl)-5,6,7,8-tetrahydro-pyrido[4,3-d]pyrimidin-4-ol (which was obtained in Intermediate 9) and methyl 4-(bromomethyl)benzoate according to Method A and Method B; LC retention time 3.25 min; MS: m/z (ESI) 494 (M-H).

What is claimed is:
1. A compound of Formula I:

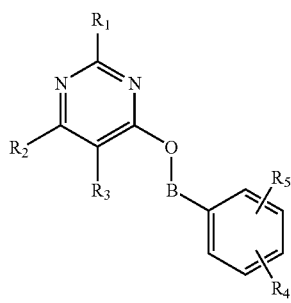

wherein:
B is alkyl of 1-4 carbons or alkoxy of 1-4 carbons;
$R_1$ is aryl optionally substituted with $R_6$;
$R_2$ is alkyl of 1-4 carbons, $CF_3$, or aryl substituted with $R_6$;
$R_3$ is H, alkyl of 1-4 carbons, $CF_3$, or aryl substituted with $R_6$;
one of $R_4$, and $R_5$ is hydrogen, halogen, alkyl of 1-4 carbons, $CO_2R_7$, $SO_2NHR_7$, $CONHR_7$, CN, $NO_2$, or $CF_3$; and the other is halogen, alkyl of 1-4 carbons, $CO_2R_7$, $SO_2NHR_7$, $CONHR_7$, CN, $NO_2$, or $CF_3$;
$R_6$ is hydrogen, halogen, $NO_2$, alkyl of 1-4 carbons, alkoxy of 1-4 carbons, alkylcarbonyloxy of 2-7 carbons, alkylcarbonyl of 2-7 carbons, $CF_3$, or COOH; and R$_7$ is hydrogen, alkyl of 1-4 carbons, or alkylaryl where the aryl group is substituted with R$_6$; or a pharmaceutically acceptable salt thereof.

2. The compound of claim 1, wherein
B is alkyl of 1-4 carbons;
R$_1$ is aryl optionally substituted with R$_6$;
R$_2$ is alkyl of 1-4 carbons, CF$_3$, or aryl substituted with R$_6$;
R$_3$ is H, alkyl of 1-4 carbons, CF$_3$, or aryl substituted with R$_6$;
one of R$_4$ and R$_5$ is hydrogen, halogen, CO$_2$R$_7$, CN, NO$_2$, or CF$_3$; and the other is halogen, CO$_2$R$_7$, CN, NO$_2$, or CF$_3$;
R$_6$ is hydrogen, halogen, NO$_2$, alkyl of 1-4 carbons, alkoxy of 1-4 carbons, CF$_3$ or COOH; and
R$_7$ is hydrogen, alkyl of 1-4 carbons, or alkylaryl where the aryl group is substituted with R$_6$; or a pharmaceutically acceptable salt thereof.

3. The compound of claim 1, which is 4-({[2-(4-chlorophenyl)-6-phenylpyrimidin-4-yl]oxy}methyl)benzoic acid.

4. A compound which is 4-[(4-fluorobenzyl)oxy]-6-phenyl-2-pyridin-4-ylpyrimidine.

5. The compound of claim 1 which is 2-(4-chlorophenyl)-4-[(4-fluorobenzyl)oxy]-6-phenylpyrimidine.

6. A compound which is 4-{[(6-phenyl-2-pyridin-4-ylpyrimidin-4-yl)oxy]methyl}benzoic acid.

7. The compound of claim 1 which is 4-{[(2,6-diphenylpyrimidin-4-yl)oxy]methyl}benzoic acid.

8. The compound of claim 1 which is 2-(3,5-dichlorophenyl)-4-[(4-fluorobenzyl)oxy]-6-isopropylpyrimidine.

9. The compound of claim 1 which is 4-[(4-fluorobenzyl)oxy]-6-isopropyl-2-(3-nitrophenyl)pyrimidine.

10. The compound of claim 1 which is 4-({[2-(3,5-dichlorophenyl)-6-isopropylpyrimidin-4-yl]oxy}methyl)benzonitrile.

11. The compound of claim 1 which is 4-({[6-isopropyl-2-(3-nitrophenyl)pyrimidin-4-yl]oxy}methyl)benzonitrile.

12. The compound of claim 1 which is 2-(3,5-dichlorophenyl)-4-isopropyl-6-{[4-(trifluoromethyl)benzyl]oxy}pyrimidine.

13. The compound of claim 1 which is 4-isopropyl-2-(3-nitrophenyl)-6-{[4-(trifluoromethyl)benzyl]oxy}pyrimidine.

14. The compound of claim 1 which is 4-({[2-(3,5-dichlorophenyl)-6-isopropylpyrimidin-4-yl]oxy}methyl)benzoic acid.

15. The compound of claim 1 which is 4-({[6-isopropyl-2-(3-nitrophenyl)pyrimidin-4-yl]oxy}methyl)benzoic acid.

16. The compound of claim 1, wherein one of R$_4$, and R$_5$ is hydrogen, and the other is CO$_2$R$_7$.

17. The compound of claim 16, wherein R$_7$ is hydrogen.

18. The compound of claim 1, wherein R$_3$ is H.

19. A pharmaceutical composition which comprises a compound of formula (I):

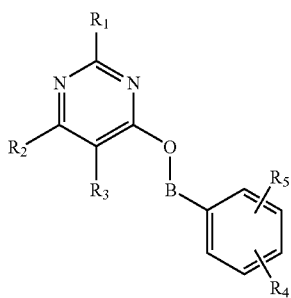

wherein:
B is alkyl of 1-4 carbons or alkoxy of 1-4 carbons;
R$_1$ is aryl optionally substituted with R$_6$;
R$_2$ is alkyl of 1-4 carbons, CF$_3$, or aryl substituted with R$_6$;
R$_3$ is H, alkyl of 1-4 carbons, CF$_3$, or aryl substituted with R$_6$;
one of R$_4$, and R$_5$ is hydrogen, halogen, alkyl of 1-4 carbons, CO$_2$R$_7$, SO$_2$NHR$_7$, CONHR$_7$, CN, NO$_2$, or CF$_3$; and the other is halogen, alkyl of 1-4 carbons, CO$_2$R$_7$, SO$_2$NHR$_7$, CONHR$_7$, CN, NO$_2$, or CF$_3$;
R$_6$ is hydrogen, halogen, NO$_2$, alkyl of 1-4 carbons, alkoxy of 1-4 carbons, alkylcarbonyloxy of 2-7 carbons, alkylcarbonyl of 2-7 carbons, CF$_3$, or COOH; and
R$_7$ is hydrogen, alkyl of 1-4 carbons, or alkylaryl where the aryl group is substituted with R$_6$; or a pharmaceutically acceptable salt thereof; and a pharmaceutical carrier.

20. A pharmaceutical composition which comprises 4-[(4-fluorobenzyl)oxy]-6-phenyl-2-pyridin-4-ylpyrimidine or 4-{[(6-phenyl-2-pyridin-4-ylpyrimidin-4-yl)oxy]methyl}benzoic acid or a pharmaceutically acceptable salt thereof; and a pharmaceutical carrier.

21. A method of treating obesity, glucose intolerance, hypertension, or ischemic diseases of the large and small blood vessels in a mammal in need thereof, wherein the obesity, glucose intolerance, hypertension, or ischemic diseases of the large and small blood vessels is associated with the occurrence of insulin resistance or hyperglycemia in the mammal, which comprises administering to said mammal, a therapeutically effective amount of a compound of formula (I):

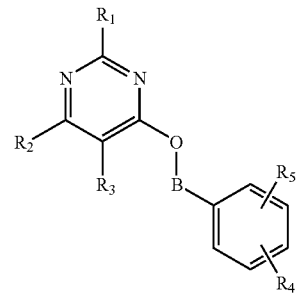

wherein:
B is alkyl of 1-4 carbons or alkoxy of 1-4 carbons;
R$_1$ is aryl optionally substituted with R$_6$;
R$_2$ is alkyl of 1-4 carbons, CF$_3$, or aryl substituted with R$_6$;
R$_3$ is H, alkyl of 1-4 carbons, CF$_3$, or aryl substituted with R$_6$;
R$_4$, and R$_5$ are each independently, hydrogen, halogen, alkyl of 1-4 carbons, CO$_2$R$_7$, SO$_2$NHR$_7$, CONHR$_7$, CN, NO$_2$, or CF$_3$;
R$_6$ is hydrogen, halogen, NO$_2$, alkyl of 1-4 carbons, alkoxy of 1-4 carbons, alkylcarbonyloxy of 2-7 carbons, alkylcarbonyl of 2-7 carbons, CF$_3$, or COOH; and
R$_7$ is hydrogen, alkyl of 1-4 carbons, or alkylaryl where the aryl group is substituted with R$_6$; or a pharmaceutically acceptable salt thereof.

22. A method of treating type II diabetes in a mammal in need thereof which comprises administering to said mammal a therapeutically effective amount of a compound of formula (I):

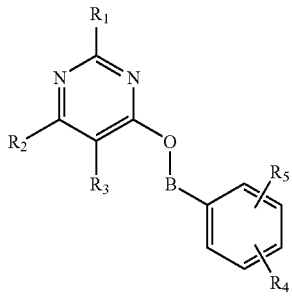

I wherein:
- B is alkyl of 1-4 carbons or alkoxy of 1-4 carbons;
- $R_1$ is aryl optionally substituted with $R_6$;
- $R_2$ is alkyl of 1-4 carbons, $CF_3$, substituted with $R_6$; or aryl
- $R_3$ is H, alkyl of 1-4 carbons, $CF_3$, or aryl substituted with $R_6$;
- $R_4$, and $R_5$ are each independently, hydrogen, halogen, alkyl of 1-4 carbons, $CO_2R_7$, $SO_2NHR_7$, $CONHR_7$, CN, $NO_2$, or $CF_3$;
- $R_6$ is hydrogen, halogen, $NO_2$, alkyl of 1-4 carbons, alkoxy of 1-4 carbons, alkylcarbonyloxy of 2-7 carbons, alkylcarbonyl of 2-7 carbons, $CF_3$, or COOH; and
- $R_7$ is hydrogen, alkyl of 1-4 carbons, or alkylaryl where the aryl group is substituted with $R_6$; or a pharmaceutically acceptable salt thereof.

23. A method of lowering glucose levels in a mammal in need thereof, which comprises administering to said mammal a therapeutically effective amount of a compound of formula (I):

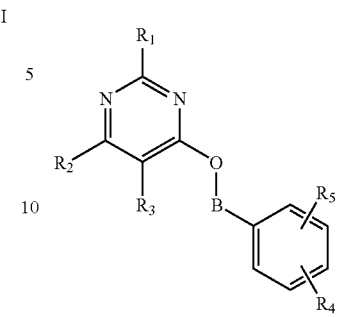

I wherein:
- B is alkyl of 1-4 carbons or alkoxy of 1-4 carbons;
- $R_1$ is aryl optionally substituted with $R_6$;
- $R_2$ is alkyl of 1-4 carbons, $CF_3$, or aryl substituted with $R_6$;
- $R_3$ is H, alkyl of 1-4 carbons, $CF_3$, or aryl substituted with $R_6$;
- $R_4$, and $R_5$ are each independently, hydrogen, halogen, alkyl of 1-4 carbons, $CO_2R_7$, $SO_2NHR_7$, $CONHR_7$, CN, $NO_2$, or $CF_3$;
- $R_6$ is hydrogen, halogen, $NO_2$, alkyl of 1-4 carbons, alkoxy of 1-4 carbons, alkylcarbonyloxy of 2-7 carbons, alkylcarbonyl of 2-7 carbons, $CF_3$, or COOH; and
- $R_7$ is hydrogen, alkyl of 1-4 carbons, or alkylaryl where the aryl group is substituted with $R_6$; or a pharmaceutically acceptable salt thereof.

* * * * *